United States Patent [19]

Heyler, III

[11] Patent Number: 4,828,560

[45] Date of Patent: May 9, 1989

[54] SPRING RING TISSUE EXPANDER

[75] Inventor: Charles J. Heyler, III, Ventura, Calif.

[73] Assignee: McGman Medical Corporation, Santa Barbara, Calif.

[21] Appl. No.: 156,717

[22] Filed: Feb. 17, 1988

[51] Int. Cl.⁴ ............................................. A61F 2/12
[52] U.S. Cl. ......................................... 623/8; 600/30; 600/31; 600/32
[58] Field of Search ...................... 128/1 R, 79, 79 A; 623/8; 600/30, 31, 32

[56] References Cited

U.S. PATENT DOCUMENTS

| 4,217,889 | 8/1980 | Radovan et al. | 128/1 R |
| 4,671,255 | 6/1987 | Dubrul et al. | 128/1 R |
| 4,685,447 | 8/1987 | Iversen et al. | 128/1 R |

Primary Examiner—Richard J. Apley
Assistant Examiner—Joe H. Cheng
Attorney, Agent, or Firm—Michael G. Petit

[57] ABSTRACT

An improved tissue expansion device for implantation beneath the skin, the improvement being the incorporation of a tensioning ring within the shell of the device. The tension ring exerts an outward force along the periphery of the shell to hold the device flat and prevent undesirable wrinkling during implantation.

14 Claims, 2 Drawing Sheets

SPRING RING TISSUE EXPANDER

BACKGROUND

Since tissue expansion was introduced over thirty years ago, the technique has become recognized as an established method of reconstruction with wide applications. Tissue expansion is used to increase the surface area of skin. The need for the technique arises when additional skin is required to repair a defect or when the overlying skin must be stretched to accommodate a large prosthesis such as a mammary implant.

Early efforts at tissue expansion utilized a simple inflatable balloon fitted under the skin in the area to be enlarged (Newmann J. Plastic & Reconstructive Surgery, 1957). It soon became apparent that such a device presented certain problems which included wrinkling of the shell during placement and a tendency for the device to expand laterally during inflation. Current art devices overcame these limitations by incorporating a base into the device which, being substantially less flexible than the thin overlying shell, tends to hold the device flat during insertion and, if reinforced as with DACRON mesh, restricts lateral expansion during inflation (See patents to Perras, Radovan).

Actually, bases have been present in tissue expansion devices ever since the dipping process of manufacturing shells has been used. In the dipping process, a mandrel shaped to the desired contour and volume of the fully expanded device, is dipped into an elastomeric dispersion and precured between successive dips. The dispersion coating the dipped mandrel runs downward toward the mandrel support during the pre-cure thus thickening the shell around the mandrel support. Since the mandrel is dipped several times to build up the shell to the desired thickness the area of the shell surrounding the mandrel support undergoes repeated thickening so that when the shell is peeled off the mandrel and the removal hole patched, the shell is unavoidably thicker in the area of the patch. Such a base, while extensible, is substantially thicker than the thin overlying shell and assists in preventing wrinkling during insertion of the device under the skin. It does little, however, to control undesired lateral expansion.

Radovan (U.S. Pat. No. 4,217,889) describes a tissue expansion device incorporating a substantially nonextensible reinforcing material into the base to control lateral expansion. The Radovan base is variously described as "stiffly flexible" and "substantially non-extensible" and as "being substantially thicker than the thin overlying cover". When a Radovan device is implanted under the skin and inflated, the overlying skin stretches as desired. The inflated shell exerts an upward pull on the margins of the device defined by the periphery of the base material causing the margin to lift upward toward the overlying skin. Because of the difference in flexibility of the cover and base, a ridge forms at the margin. Such marginal uplifting can exert undue pressure against the thin overlying skin with necrosis and subsequent erosion.

Surprisingly, it is found that by incorporating a marginal tensioning ring into the interior chamber of a shell of substantially uniform thickness; that is, as uniform a thickness as is possible using the dipping technique to make the shell, that the resultant device has all the desired operative properties of current art devices, e.g. removal of wrinkles from the shell, ease of placement, control of lateral expansion, and demonstrates minimal tendency toward undesired marginal uplifting.

It is one object of the present invention to provide a tissue expansion device which contains all the desired aforesaid attributes of current art devices and present a further attribute of reducing tissue damage due to marginal uplifting. It is a further object of this invention to provide a relatively inexpensive tissue expansion device.

DESCRIPTION OF THE INVENTION

Figure 1:
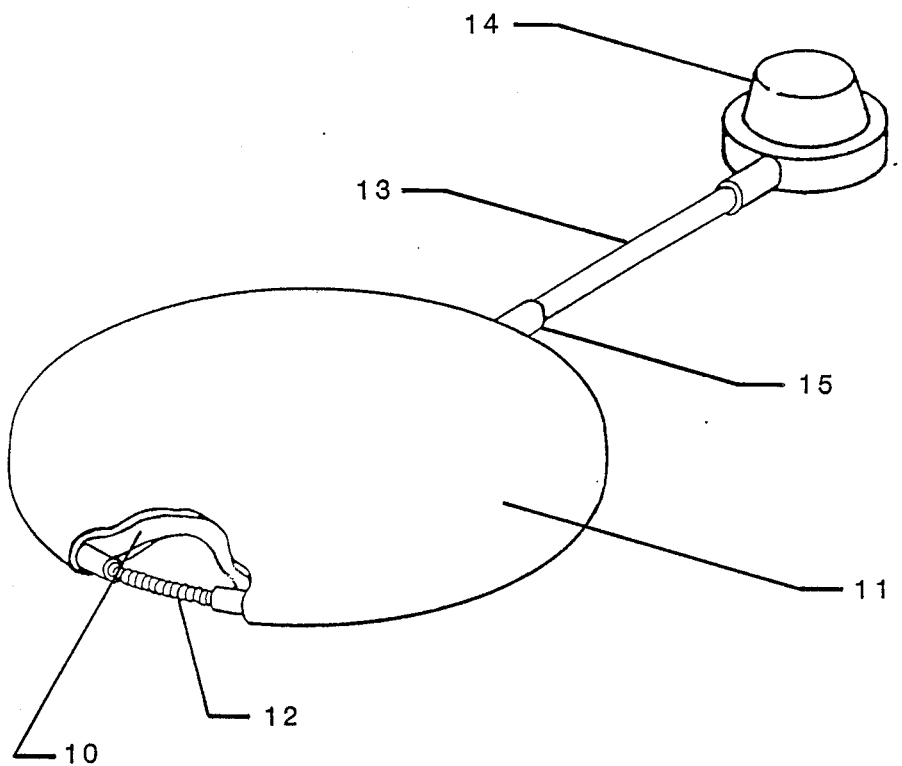
FIG. 1 is a cutaway perspective view of one embodiment of the present invention wherein the marginal tensioning ring is circular and the injection reservoir is remote from the shell.
Figure 2:
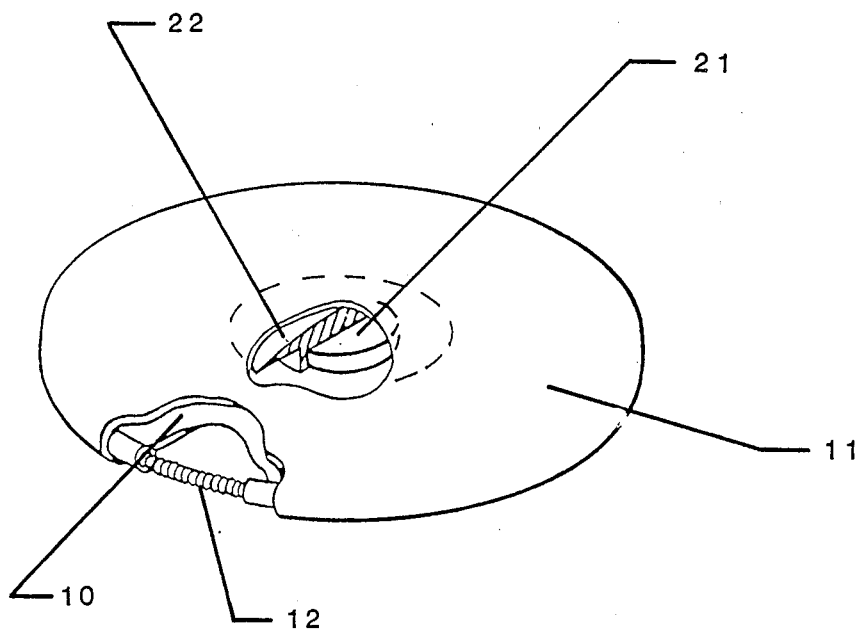
FIG. 2 is a cutaway view as in FIG. 1 except that the injection reservoir is integral with the shell.

In its simplest conceptual form, an embodiment of the present invention can be viewed as a shell stretched over a tensioning ring as shown in FIG. 1. FIG. 1 is a perspective view of the device showing a thin shell (11) stretched over a tensioning ring (12) to form a substantially drum-shaped tissue expander. A fill tube (13) enters the interior leakproof chamber (10) defined by the shell (11) through an opening provided in the shell (15) and is inflated by the injection of a desired quantity of fluid into the chamber by means of an injection reservoir (14) comprising a second sealed chamber in fluid communication with the leakproof chamber (10) defined by the shell and a self-sealing septum. FIG. 2 is the same as FIG. 1 except that the injection reservoir (21) is integral with the shell and surrounded by a reinforcing patch (22) which further prevents the shell from folding over the injection reservoir.

The device of FIG. 2 can be conveniently made using a dipping process for shell buildup and simultaneous incorporation of the tensioning ring. A molded silicone "O" ring or silicone tubing is fitted over a pulley-shaped mandrel that has been pre-coated with a releasing agent. The mandrel fitted with the tensioning ring is then repeatedly immersed in a dipping tank containing an elastomeric dispersion (silicone is desirable) until the shell builds up to the desired thickness (usually 0.020" is sufficient) then vulcanized. A hole is cut around the mandrel supporting rod to facilitate removal of the vulcanized shell from the mandrel. The shell and tensioning ring are peeled from the mandrel as a single unit and the hole covered with a patch housing an injection reservoir. The patch may be applied by using a biocompatible elastomeric adhesive or it may be vulcanized to the shell.

Alternatively, as in the device of FIG. 1, a circular loop of elastomeric tubing which may have a plurality of openings about the inner circumference is out to receive a "tee" coupling or a four-way coupling to permit fluid communication between the injection reservoir and the leakproof interior chamber defined by the shell ((11), FIG. 1) through the fill tube (13). The three way coupling (not shown) or four way coupling (not shown) may be fabricated from any biocompatible material such as TEFLON DELRIN or 316L stainless steel. After the tubing and fill tube are joined or spliced together via the appropriate coupling, the assembly may be fitted onto the mandrel as described earlier. Repeated dipping of the splice thus formed during shell buildup provides a leakproof seal between the fill tube and the shell interior.

It is desirable to use a filament of spiral wound wire such as 316L stainless steel to provide additional tensioning of the loop described above. The spiral wound wire, usually wound to a density of 20 turns per inch of 20 gauge wire and to a spiral diameter between ⅛ inch and ¼" depending on the size of the device, is inserted into a length of silicone tubing and the ends drawn together as in FIGS. 1 and 2 to form a loop (12) which, while capable of distortion, will provide a restoring force directed outward until a position of minimum potential energy is reached. At this point, the outward force exerted on the tubing is balanced by the compressional force created in the inner wall of the tubing.

It is obvious from the foregoing that many variations on the shape of the device are possible by changing the shape of the mandrel and molded marginal tensioning loop.

Alternatively, the shell may be dipped via a mandrel, removed from the mandrel as discussed previously, and the marginal tensioning loop inserted into the shell through the hole in the shell before the patch is applied and a fill tube cemented to the shell or otherwise attached by means well known in the art.

Figure 3:
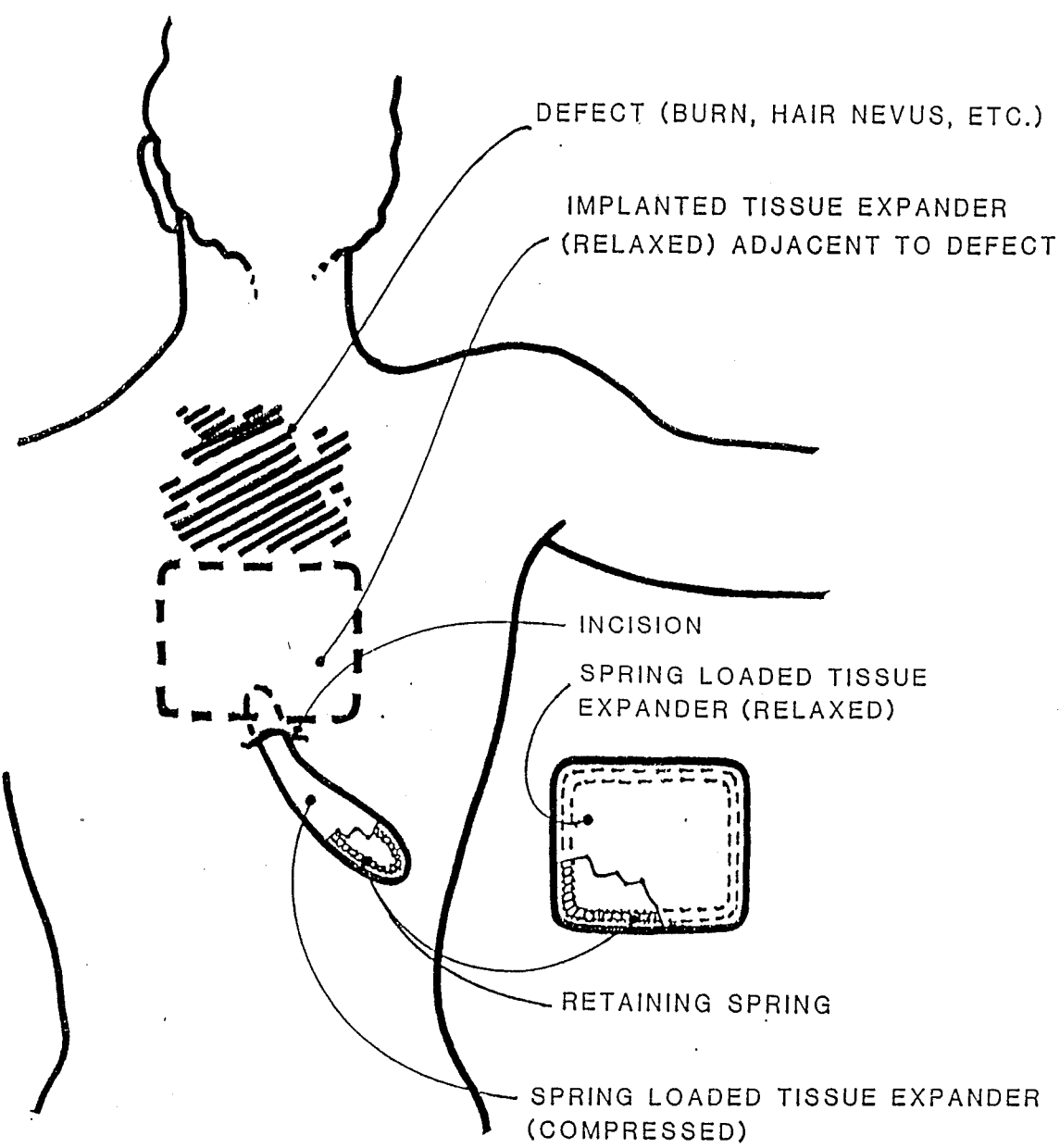
FIG. 3 depicts an example of placement of an embodiment of the device of the present invention beneath the skin of a patient to expand the skin contiguous with a defect.

The device of the present invention may be used to generate a skin flap for plastic or reconstructive surgery as shown in FIG. 3. First a pocket is made underneath the skin to house the tissue expander. The expander is then inserted into the pocket via an incision in the skin and permitted to relax into the pocket thereby removing wrinkles from the shell. A fluid is then injected into the injection reservoir until expansion of the overlying skin has been completed.

The present invention provides a tissue expansion device with a smoothly contoured margin determined by the curvature and diameter of the marginal tensioning loop which is easy to place, wrinkle free and resists exerting undue marginal pressure on the overlying skin during expansion. It does not exhibit substantial lateral expansion during inflation and is relatively inexpensive to manufacture.

What I claim is:

1. A tissue expansion device for implantation beneath the skin, thereafter to be expanded to enlarge the surface area of the skin overlying the device, comprising:
    (a) a shell consisting of a thin flexible, expandable elastomeric envelope of substantially uniform thickness containing a substantially leakproof chamber therein;
    (b) a spring loaded marginal tensioning loop, said tensioning loop disposed within said leakproof chamber to exert a substantially uniform outward pressure against the interior wall of said shell, said outward pressure being sufficient to stretch said shell at least enough to remove wrinkles from said shell; and
    (c) means for introducing a fluid into said leakproof chamber.

2. The tissue expansion device of claim 1 wherein said elastomeric envelope is silicone.

3. The tissue expansion device of claim 1 wherein said spring loaded marginal loop consists of a spiral wound filament, the free ends of said spiral wound filament being drawn substantially together.

4. The tissue expansion device of claim 3 wherein said spiral wound filament is encased in a biocompatible elastomer.

5. The tissue expansion device of claim 4 wherein said biocompatible elastomer is silicone.

6. The tissue expansion of claim 3 wherein said filament consists of at least one strand of a biocompatible metal.

7. The tissue expansion device of claim 8 wherein said biocompatible metal is 316L stainless steel.

8. The tissue expansion device of claim 4 wherein said filament consists of at least one strand of a biocompatible plastic.

9. The tissue expansion device of claim 1 wherein said spring loaded marginal loop comprises a "O" shaped silicone ring.

10. The tissue expansion device of claim 1 wherein said spring loaded marginal loop comprises a molded silicone filament of cross sectional diameter substantially greater than the thickness of said shell.

11. A tissue expansion device for implantation beneath the skin, thereafter to be expanded to enlarge the surface area of the skin overlying the device, comprising:
    (a) a shell consisting of a thin, flexible, expandable elastomeric envelope of substantially uniform thickness containing a substantially leakproof chamber therein;
    (b) a spring loaded marginal loop contained within the interior of said chamber, said marginal loop providing tension directed radially outward against the interior surface of said shell, said tension being sufficient to remove substantially all wrinkles from the surface of the shell; and
    (c) means for introducing a fluid into said leakproof chamber.

12. The device of claim 11 wherein said means for introducing a fluid into said chamber comprises an injection reservoir in fluid communication with the interior of said chamber.

13. The device of claim 12 wherein said injection reservoir is located upon the surface of said shell.

14. The device of claim 15 wherein the portion of said shell surrounding said injection reservoir is reinforced.

* * * * *